United States Patent [19]
Pellow et al.

[11] Patent Number: 4,866,106
[45] Date of Patent: Sep. 12, 1989

[54] ANTIFOULING COMPOSITION

[75] Inventors: Scott P. W. Pellow, North Vancouver; Barry S. Larkman; Paul Stovicek, both of Coquitlam, all of Canada

[73] Assignee: Waitomo Industrial Investments Ltd., Canada

[21] Appl. No.: 271,530

[22] Filed: Feb. 8, 1988

[51] Int. Cl.$^4$ ............................................... C08K 5/19
[52] U.S. Cl. ..................................... 523/122; 523/461; 524/257
[58] Field of Search ................. 523/122, 461; 524/257

[56] References Cited

U.S. PATENT DOCUMENTS

| | | | |
|---|---|---|---|
| 3,285,959 | 11/1966 | McFarlane | 524/257 |
| 3,337,352 | 8/1967 | Sano et al. | 523/122 |
| 3,854,960 | 12/1974 | Plum et al. | 106/15 |
| 3,896,753 | 7/1975 | Shepherd et al. | 523/122 |
| 4,128,429 | 12/1978 | Wyant et al. | 106/15 |
| 4,383,053 | 5/1983 | Honda | 523/122 |
| 4,552,885 | 11/1985 | Gabriele et al. | 514/315 |
| 4,631,302 | 12/1986 | Supcoe et al. | 523/122 |
| 4,661,400 | 4/1987 | Guglielmo | 428/255 |
| 4,675,051 | 6/1987 | Baxter | 106/18.32 |
| 4,687,792 | 8/1987 | Russell et al. | 523/177 |
| 4,711,915 | 12/1987 | Doe | 523/122 |
| 4,752,629 | 6/1988 | Proudlock et al. | 523/122 |

FOREIGN PATENT DOCUMENTS

| | | |
|---|---|---|
| 124538 | 10/1978 | Japan . |
| 210677 | 10/1985 | Japan . |
| 217274 | 10/1985 | Japan . |
| 84167 | 4/1987 | Japan . |
| 232470 | 10/1987 | Japan . |
| 8462 | 1/1988 | Japan . |
| 81177 | 4/1988 | Japan . |

Primary Examiner—Lewis T. Jacobs
Attorney, Agent, or Firm—Bert J. Lewen; Beth Kovitz; Henry Sternberg

[57] ABSTRACT

An antifouling coating composition comprising a settable resin and a non-metallic algicide that does not react with the resin. The composition can be applied to flexible and rigid substrates and does not contain heavy metals.

4 Claims, No Drawings

ANTIFOULING COMPOSITION

FIELD OF THE INVENTION

This invention relates to an antifouling coating composition. The composition is useful for coating equipment to be inserted in the sea, for example fish nets and boat hulls but also finds use for coating roof shingles and the like exposed to much rain and subject to algae growth.

DESCRIPTION OF THE PRIOR ART

The growth of algae on structures, for example on boat hulls, on fishing nets, on roofs and on patios is unsightly. There are however, more important failings. The hull of a boat is considerably less efficient when coated with algae. The drainage of a roof can be adversely effected by the presence of algae and patios, balconies and the like can become slippery when wet if algae is present. In industry fouling and plugging of water pipes, particularly in cooling systems, can occur with algae growth, for example in the pulp and paper mill industries. The warm temperatures in cooling system waters make ideal conditions for algae growth.

A hull of a boat or a walkway can be scrubbed to remove the algae but, for example, in the case of a boat, this involves removing the boat from the water and also involves a considerable amount of hard work. As a result chemical approaches have been used. Compounds such as chlorine, organic mercury compounds, chlorinated phenols, organic bromine compounds and organic sulphur compounds have all been used in an attempt to reduce the growth of algae.

In the growing of fish in pens there is a marked need for a biodegradable antifouling coating for the nets that are used to pen the fish. The coating is required to prevent the growth of marine organisms, which restrict the flow of fresh tidal water through the net.

This need has been met by the use of antifouling coatings containing heavy metals, for example organic tin and mercury compounds and the like. However, heavy metal coating are environmentally undesirable, particularly in the marine environment. It has been shown that they have an adverse effect upon shell fish beds and other coastal marine life even in trace amounts. As a result the use of heavy metals for this use is now illegal in some jurisdictions.

Yet a further use of antifouling compositions is in hospitals where medically sterile environments are required if staff infections are to be avoided.

However, no system developed so far is believed to be ideal. The most popular, the use of chlorine, is limited first by the toxicity of chlorines and chlorine containing compounds. To be effective chlorine requires quite large doses, making its use economically unattractive. Furthermore, chlorine is a highly reactive compound, meaning that it can be difficult to store and, when applied, can react with other compounds in the environment, reducing its effectiveness against algae.

U.S. Pat. No. 3,881,008 to Shema et al. teaches the use of N-2-nitrobutyl morpholine mixed with N-alkyl-dimethyl-benzyl ammonium chloride as a slime control composition. But the prior art fails to teach coating compositions, effective over a considerable period, to destroy algae.

SUMMARY OF THE INVENTION

The present invention seeks to provide a lasting coating composition, giving antifouling properties over a considerable period. Accordingly the present invention is an antifouling coating composition comprising:
a settable resin; and
a non-metallic algicide that does not react with the resin.

The resin may be a polymer of an olefinic monomer, suspendable in water to form a stable emulsion or latex. For example, suitable polymers include vinyl acetate-acrylic copolymer; vinyl acetate-ethylene copolymer; acrylic-polyvinyl chloride copolymer and vinylidene chloride copolymers.

In a further preferred embodiment the settable resin may be an epoxy resin, for example one curable by a polyamide.

The preferred non-metallic algicides are quaternary ammonium compounds. Particularly preferred are n-alkyl dimethyl benzyl ammonium chlorides. Especially preferred are those compounds in which the n-alkyl group is one having 12, 14 or 16 carbon atoms.

Other useful quaternary ammonium compounds include myristyl dimethyl benzyl ammonium chloride, stearyl dimethyl benzyl ammonium chloride, dialkyl benzyl ammonium chlorides, and N-trichloromethyl thiophthalimide.

A composition according to the invention may include a filler, for example calcium carbonate, talc or silica. The use of fillers as a means of increasing the bulk of coating composition is well-known.

DESCRIPTION OF THE PREFERRED EMBODIMENTS

The invention is illustrated in the following formulations, which illustrate antifouling compositions according to the present invention, particularly useful for coating fish nets.

Formula A 2 parts UCAR TM 503 polymer (acrylic-styrene)
0.1 to 1.25 parts N-alkyl dimethylbenzyl ammonium chloride (e.g. from Lonza, N.J.)
0 to 6 parts water Add the polymer slowly with stirring to the water until well mixed. Continue stirring and slowly add the algicide until well mixed. Coating composition thickness is easily controlled by reducing or increasing water content. Lower water content results in thicker coatings. This composition containing 6 parts water is particularly good for coating fish netting to prevent fouling.

Formula B 2 parts Swift 6113 polymer (vinyl acetate-ethylene) from Swift Co., Burnaby, Canada
0.1 to 1.25 parts N-alkyl dimethylbenzyl ammonium chloride
0 to 6 parts water This formula containing 1.2 parts algicide is particularly good for coating fish netting to prevent fouling.

Formula C

Same as formulas A or B but polymer is vinyl-acetate type such as Union Carbide 367.

Formula D

Same as formulas A or B but polymer is Reichold 101X from Reichold, Port Moody, Canada

Formula E

Same as formulas A or B but polymer is vinyl alcohol-vinyl acetate type such as UCAR 137.

Formula F

Same as formula A or B but polymer is acrylic-styrene-polyvinyl alcohol type such as UCAR 516 or UCAR 124.

Formula G

Same as formulas A or B but polymer is natural rubber.

Formula H 25 parts polymer of types shown in formulas A to G above
74 parts or less of water
1 part algicide or microbicide such as FUNGITROL 11 (formulation containing Folpet produced by Nuodex Inc., Piscataway, N.J. Folpet is a trademark for N-trichloromethyl thiophthalimide.

This formula is blended in analogous fashion to formula A above.

Formula I

Same as formulas A to H but N-alkyl n-methyl ammonium chlorides having any combination of carbon containing alkyl groups, or dialkyl groups, or stearyl containing groups, or methyl containing groups or aryl containing groups are used as algicide or microbicide.

Formula J

Same as formulas A to I with the addition of varying amounts of polymer stabilizers such as Dow Corning 6020 or 6070 or 6075 silane. These stabilizers increase the ability of the coating composition to repel water.

The above formulas A to J can be used immediately or stored and then remixed, with stirring, prior to coating a marine surface, for example a fish net. In this application fish nets can be dipped in these formulas followed by draining and drying in air for, for example, 90 minutes. Good coatings are especially achieved in temperatures of at least 18° C. Coating should be carried out in a well ventilated environment, encouraging good air flow. The coated surface can be water rinsed prior to use in the marine environment. Coatings typically have a life of about 18 months and can be reapplied by washing the used coatings with pressurized water followed by redipping of the re-exposed substrate, for example fish net, using the method described above.

Epoxy containing formulations are illustrated by formulas K, L and M below. A highly water resistant epoxy, for example that available under the trade mark Novolac Den 444 from Dow Chemical, can be mixed with a variety of solvents to form a new composition referred to as part A in these formulations. Polyamides such as those available from Henkel under the trade mark Versamide 115, 125 and 140 can be dispersed in a solvent, for example xylene, and then mixed with the above algicides to form novel water, free antifouling dispersions referred to as part B in the formulations below. Parts A and B can be mixed to form antifouling compositions, which set due to the reaction between the epoxy bases and the polyamides. Various types and amount of solvents are chosen to complement the viscosity characteristics of the amide hardener and the epoxyresin. Solvents can be evaporated as the reaction proceeds. Parts A and B are mixed in the proportions of 3 to 1 for formulas K and M. Parts A and B are mixed in the proportions of 2.3 to 1 for formula L. The ratio is dependent on stoichiometric requirements plus flexibility and adhesion requirements. After waiting 10 to 15 minutes the product of A and B can be used to coat the desired substrate. Useable application times are typically 2 hours.

| Composition of Clear* Epoxy-Antifouling Compositions in Parts by Weight | | | |
|---|---|---|---|
|  | Formula K | Formula L | Formula M |
| Part A |  |  |  |
| Novolac Den 444 | 100 | 100 | 100 |
| Methyl isobutyl ketone | 70 | 70 | 70 |
| Propylene glycol methyl ether | 40 | 40 | 40 |
| Xylene | 80 | 0 | 80 |
| Urea formaldehyde | 1.5 | 1.5 | 1.5 |
| Fungitrol 11 | 4–8 | 4–8 | 4–8 |
| Part B |  |  |  |
| Versamide 115 | 82 | 0 | 82 |
| Xylene | 35 | 17 | 17 |
| Versamide 140 | 0 | 67 | 0 |
| Barquat MS 100 | 0 | 0 | 4–190 |
| Dow Corning 6020 Silane | 1–5 | 1–5 | 1–5 |

*fillers and colorants can be added to part A as required

Thus the present invention provides low toxicity, antifouling compositions particularly suitable for coating marine submersibles, for example fish nets and boat hulls, and containing non-metallic algicide. The compositions are also useful for coating non-marine structures, such as roof shingles, particularly those exposed to much rain and thus subject to algae growth.

Formulations according to the present invention may also be useful in the treating of cedar shakes and shingles. In addition to the antifouling capabilities it also has the ability to confine or contain cedar oils within the shake or shingle. This prevents the contamination of water courses by the migration of the oil from the wood. This migration is a problem in the development of large subdivisions.

The compositions are characterized by the absence of chemical reaction between the algicide and the carrier. The algicide is encapsulated in the polymer carrier and slowly migrates to the surface to give a long term, reliable antifouling effect.

The quarternary ammonium chloride algicides, leaching into the surrounding waters from the polymer carrier, are degraded by oxygen and water, unlike highly toxic metal containing antifouling agents. Algicides of the N-trichloromethyl thiophthalmide type, which are generally available under the trade mark Folpet leach into the surrounding waters and are slowly hydrolysed. The chlorine substituents are combined with marine cations such as sodium, potassium, calcium and magnesium to form harmless salts.

The use of inert fillers which are desirable in coating formulations, does not have any effect on the antifouling capability of the compositions.

The algicides act as plasticizers for the polymer carriers, making the latex containing coatings particularly suitable for flexible substrates by inhibiting chipping of the polymer from the substrate, for example fish nets. Epoxy containing coatings are particularly suitable for rigid substrates, such as marine buoys or boat hulls. Algicides impregnated in epoxy carriers leach less rapidly than algicides contained in latex carriers.

I claim:

1. An antifouling coating composition for submergible articles comprising a polymer selected from a vinyl acetate homopolymer; a vinyl acetate-acrylic copolymer; a vinyl acetate-ethylene copolymer; and an acrylic polyvinyl chloride copolymer; and a non-metallic algicide consisting essentially of a quaternary ammonium compound having methyl groups and two alkyl groups alone or in combination with a second quaternary ammonium compound having methyl groups, an alkyl group and a benzyl group, said algicide being encapsulated in said polymer and being capable of being leeched from said composition during submersion.

2. The composition of claim 1 wherein the polymer is a vinyl acetate-ethylene copolymer and the alkyl group in the quaternary ammonium compound has up to 16 carbon atoms.

3. A composition as claimed in claim 1 including a filler.

4. A composition as claimed in claim 3 in which the filler is selected from calcium talc, silica.

* * * * *

UNITED STATES PATENT AND TRADEMARK OFFICE
CERTIFICATE OF CORRECTION

PATENT NO. : 4,866,106
DATED : September 12, 1989
INVENTOR(S) : Paul Stovicek

It is certified that error appears in the above-identified patent and that said Letters Patent is hereby corrected as shown below:

On the title page:

Item [21]  Change "271,530" to --"153,010"--.

Item [75]  Delete "Scott P.W. Pellow, North Vancouver; Barry S. Larkman;"

Item [75]  "both of" and "all of".

Signed and Sealed this

Twenty-second Day of January, 1991

Attest:

HARRY F. MANBECK, JR.

*Attesting Officer*       *Commissioner of Patents and Trademarks*

UNITED STATES PATENT AND TRADEMARK OFFICE
CERTIFICATE OF CORRECTION

PATENT NO.   :   4,866,106
DATED        :   Sept. 12, 1989
INVENTOR(S)  :   Paul Stovicek It is certified that error appears in the above-identified patent and that said Letters Patent is hereby corrected as shown below:

On the title page, below "United States Patent [19]": delete "Pellow et al." and substitute --Stovicek--.

Signed and Sealed this

Eighth Day of December, 1992

Attest:

DOUGLAS B. COMER

Attesting Officer

Acting Commissioner of Patents and Trademarks